United States Patent [19]

Toya

[11] Patent Number: 5,068,091

[45] Date of Patent: Nov. 26, 1991

[54] DEVICE FOR DYEING TISSUES FOR IMMUNE RESPONSE OBSERVATION

[75] Inventor: Matsumi Toya, Koushoku, Japan

[73] Assignees: Kabushiki Kaisha Tiyoda Seisakusho, Koushoku; Sakura Finetechnical Co., Ltd., Tokyo, both of Japan

[21] Appl. No.: 314,374

[22] Filed: Feb. 22, 1989

[30] Foreign Application Priority Data

Feb. 22, 1988 [JP] Japan .................................. 63-21239

[51] Int. Cl.$^5$ .............................................. B01L 3/00
[52] U.S. Cl. ....................................... 422/99; 422/63; 422/102; 422/104; 118/410
[58] Field of Search ................... 422/102, 104, 63, 99; 118/410

[56] References Cited

U.S. PATENT DOCUMENTS

| | | |
|---|---|---|
| 3,667,896 | 6/1972 | McCormick . |
| 4,181,501 | 1/1980 | Keese et al. ........................... 422/102 |
| 4,451,433 | 5/1984 | Yamashita et al. ..................... 422/64 |
| 4,775,003 | 10/1988 | Koh ...................................... 422/104 |

FOREIGN PATENT DOCUMENTS

62-314192  6/1989  Japan .
2216261  10/1989  United Kingdom .

Primary Examiner—David L. Lacey
Assistant Examiner—Abanti B. Singla
Attorney, Agent, or Firm—Ladas & Parry

[57] ABSTRACT

A device for dyeing tissues of living bodies for immune response observation comprises dyeing block on which are formed a plurality of adjoining base portion each having a flat upper surface. On one side of the base portion is formed a ridge, and on the other side of the base portion is formed a supporting surface which is slightly higher than the ridge. A slide glass having a tissue attached to one surface is placed above each of the base portion with the surface thereof facing the upper surface of the base portion, so as to bridge the ridge and the supporting surface in such a manner that a thin wedge-shaped gap is defined between the upper surface of the base and the undersurface of the slide glass. Dyeing liquid is dripped from above onto the upper surface of the base portion which is not covered by the slide glass. The dripped dyeing liquid spreads into the wedge-shaped gap by capillary action, whereby the tissue on the undersurface of the slide glass is dipped in the liquid and dyed. For cleaning the base portion and the slide glass after the dyeing operation, cleaning liquid is supplied on the base portion through a port formed therein. The waste liquid is exhausted through an exhaust port formed in the upper surface and an exhaust pipe connected to the exhaust port. Waste liquid channels are provided adjacent to the base portion.

12 Claims, 5 Drawing Sheets

DEVICE FOR DYEING TISSUES FOR IMMUNE RESPONSE OBSERVATION

BACKGROUND OF THE INVENTION

The present invention relates to a device for dyeing tissues of organisms for immune response observation, which is used at hospitals or the like for dyeing a piece of tissue taken from a living body in order to diagnose cancer.

There have been practiced diagnoses of cancer or the like by utilizing the immune response of antigen-antibody reactions.

In the case of diagnosis utilizing such immune response, a piece of tissue taken from a living body is attached to a slide glass and is brought into contact with treatment liquids (to be referred to as "dyeing liquids" hereinafter) in a predetermined sequence, thereby dyeing the piece of tissue.

However, when the piece of tissue is subjected to the dyeing process for immune response observation for the above-mentioned objects, the following problems arise.

That is, in the case of the automatic dyeing process so far carried out, a dyeing liquid is first poured into a beaker-shaped vessel, and then a slide glass to which is attached a piece of tissue is dipped into the dyeing liquid in the vessel so as to be brought into contact with the dyeing liquid. By doing so, a relatively large quantity of dyeing liquid must unavoidably be used. The dyeing liquids used for the observation of immune response are very expensive so that it is desirable to reduce the quantity of a dyeing liquid used to a minimum.

Because of the reason described above; that is, in order to reduce the cost of the process for dyeing pieces of tissue for immune response observation, the dyeing process has been carried out manually in most cases, but the dyeing process takes a relatively long period of time so that in some cases it must be carried out throughout the night. Therefore, such manual dyeing process is not desirable from the viewpoint of health and working conditions.

In view of the above, the primary object of the present invention is to provide a device for dyeing a piece of tissue for immune response observation which can carry out the process of dyeing tissues with a small quantity of a dyeing liquid in a positive and reliable manner whereby the above and other problems encountered in the conventional tissue dyeing processes can be substantially solved.

For the above and other objects, a device for dyeing tissues for immune response observation according to the present invention comprises: flat base means with a substantially horizontal upper surface; means for supporting above said upper surface a slide glass with the undersurface thereof facing said upper surface and with the undersurface having a tissue attached thereto, said supporting means being formed relative to the base means to provide a thin wedge-shaped gap between said upper surface and said undersurface of the slide glass; and means for supplying a dyeing liquid into said gap.

The means for supporting the slide glass may comprise a ridge disposed on one side of the base means, and a support surface provided on the other side of the base means, the support surface being slightly higher than the top of the ridge.

In the case of carrying out the tissue dyeing process by utilizing the device with the above-described construction in accordance with the present invention, the slide glass having on its undersurface a piece of tissue to be dyed is placed in position above the flat base means so as to bridge the ridge and the supporting surface in such a way that the piece of tissue on the slide glass is in opposing relationship with the upper surface of the base portion. Under the above-described condition, a thin wedge-like gap which is converging in a direction from the ridge to the supporting surface is defined between the undersurface of the slide glass and the upper surface of the base portion.

After the bridging of the ridge and the supporting surface by the slide glass, one or more drops of a predetermined dyeing liquid are dripped onto the surface of the base portion not covered by the slide glass. Because of the thin wedge-like gap, one or more drops of the dyeing liquid supplied onto the exposed surface of the base portion spread through the gap by capillary action and are brought in intimate contact with the piece of tissue on the undersurface of the slide glass. In other words, the piece of tissue is dipped into the dyeing liquid within the gap.

After the piece of tissue on the undersurface of the slide glass is brought into contact with the dyeing liquid for a predetermined length of time, the used dyeing liquid exhaust means which has been in the de-energized state is energized so that the used dyeing liquid is exhausted through a discharge port opened adjacent to the ridge in the upper surface of the base portion. After exhausting the used dyeing liquid, the exhaust means is de-energized and then cleaning liquid supply means which has been maintained in the de-energized state, is energized for a predetermined period of time so that the cleaning liquid is discharged through a discharge port opened in the upper surface of the base portion adjacent to the ridge. The cleaning liquid supplied in the manner described above spreads through the gap between the undersurface of the slide glass and the upper surface of the base portion by capillary action, thereby cleaning the dyeing liquid attached to the piece of tissue on the slide glass.

After the completion of the cleaning step for a predetermined period of time, the waste liquid exhaust means is energized again so that the used cleaning liquid in the gap is exhausted out of the device. Thereafter, the next dyeing liquid dripping step is started.

The above-stated steps are repeated so that a series of tissue dyeing process is accomplished.

Embodiments of the present invention will now be described below in detail with reference to the drawings.

DETAILED DESCRIPTION OF THE PREFERRED EMBODIMENTS

Figure 1:
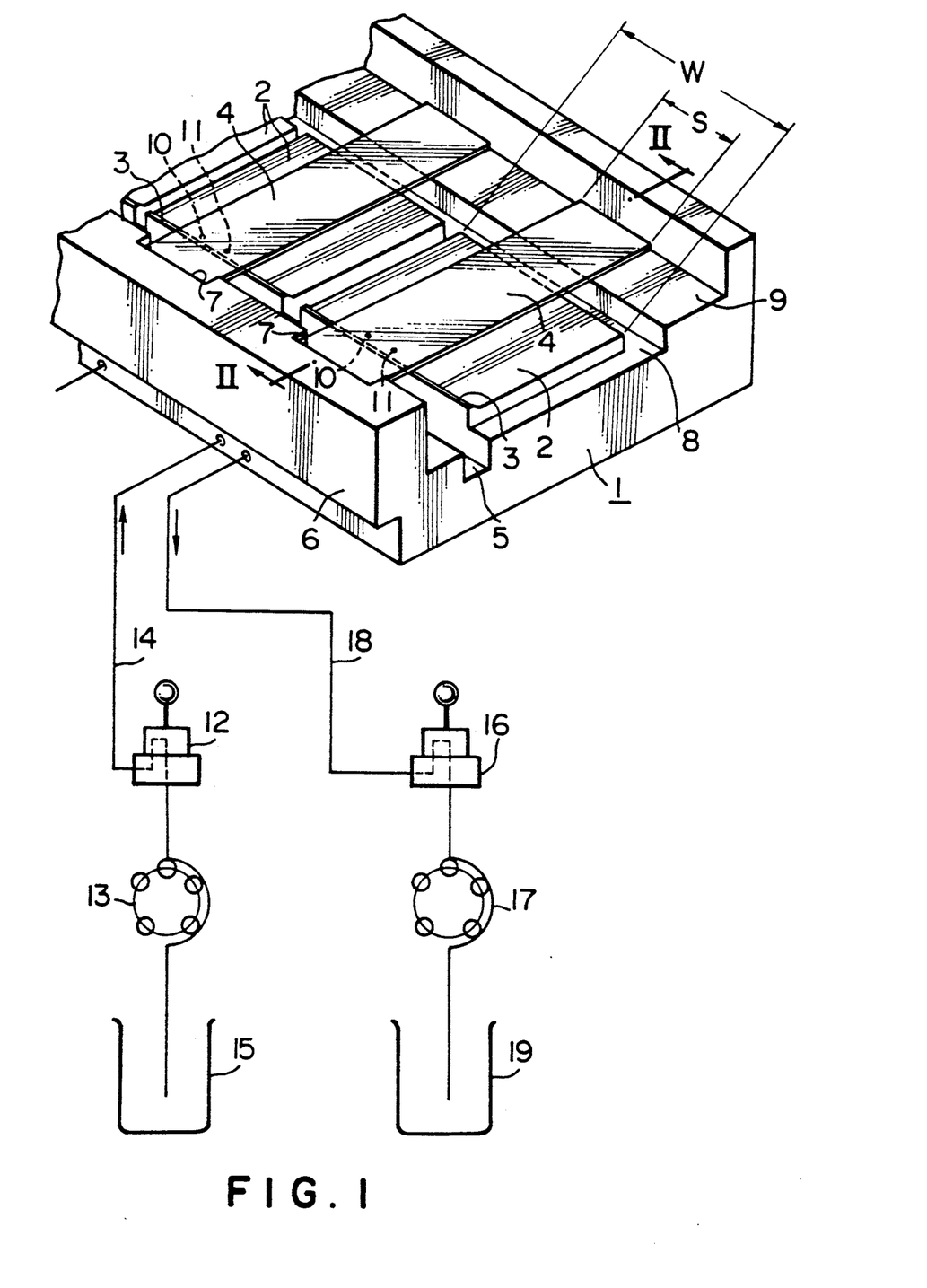
FIG. 1 is a perspective view of a device for dyeing tissues for immune response observation with a treatment liquid dripping device removed in accordance with the present invention.

With reference to FIG. 1, the device according to the present invention has a dyeing block 1 made of aluminum or the like. The block 1 has flat base portions 2 arranged side by side on the upper surface thereof, and a ridge 3 of a small height of the order of 0.2 mm is formed along one side of each base portion 2 throughout the whole width thereof. The width W of each base portion 2 is greater than the width S of a slide glass 4. As is well known, the slide glass 4 has attached thereto a piece of tissue. As shown, when the center portion of the slide glass 4 is mounted on the base portion 2, both the side portions in the lengthwise direction of the base portion 2 extend and are exposed beyond the two side edges of the slide glass 4 in the same direction.

A bank 6 forms an integral part of the dyeing block 1 and extends in parallel opposed relation to the ridge 3. A waste liquid channel 5 is formed between the ridge 3 and the wall 6, while a recess 7, which can snugly receive therein one end of each slide glass 4, is formed in the upper and inner surfaces of the bank 6 so that when each slide glass 4 is mounted on each base portion 2, its position is correctly determined and maintained.

Figure 2:
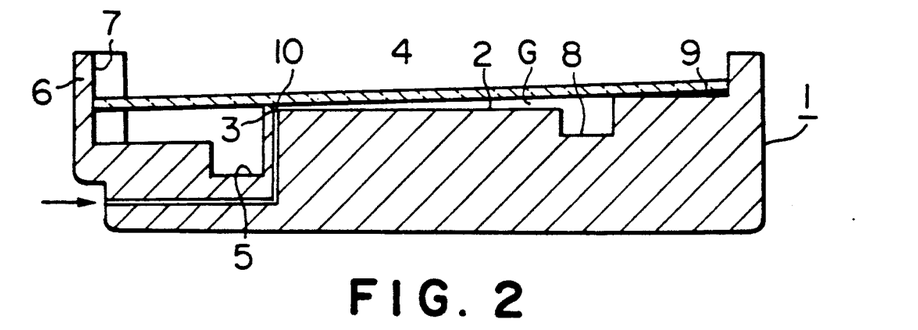
FIG. 2 is a sectional view taken along the line II—II of FIG. 1.

A raised supporting surface 9 is formed on the block 1 in parallel opposing relationship to the bank 6. The supporting surface 9 is located on the side opposite to the side where the bank 6 is formed. Another waste liquid channel 8 is formed alongside the supporting surface 9. The portion 9 is adapted to support the other end portion of the slide glass 4 mounted on the base portion 2. The supporting surface 9 is slightly higher than the ridge 3 so that each slide glass 4 which is supported by the ridge 3 and the supporting surface 9 is slightly downwardly inclined in the direction from the supporting surface 9 to the ridge 3 as shown in FIG. 2. The angle between the slide glass 4 and the horizontal is, for instance, one degree (1°).

Figure 3:
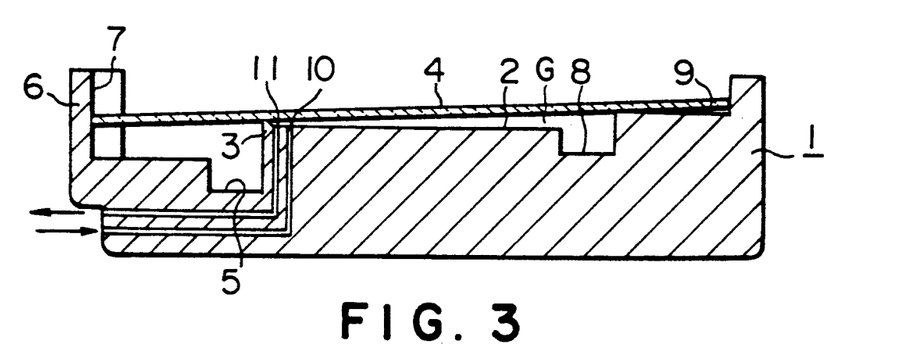
FIG. 3 is a view similar to FIG. 2 but illustrating the arrangement of a supply port and an exhaust port.

A liquid discharge port 10 and a liquid exhaust port 11 are opened in the upper surface of each base portion 2 adjacent to the ridge 3, as shown in FIGS. 1 and 3. The discharge port 10 communicates through a discharge pipe 14 having a feed pump 13 and a rotary selection valve 12 with a cleaning liquid storage tank 15. This line system constitutes a cleaning liquid supply means which discharges a cleaning liquid into the dyeing block 1. According to the present invention, the rotary selection valve 12 is used to feed the cleaning liquid to a selected piece of tissue among a plurality of pieces of different kinds of tissues on a plurality of slide glasses 4 to be dyed. The rotary selection valve 12 can be eliminated when a plurality of pieces of tissue are not dyed.

The exhaust port 11 communicates through an exhaust pipe 18 having a rotary valve 16 and an exhaust pump 7 with a waste liquid tank 19. Thus, this system constitutes a waste liquid (including the used cleaning liquid) exhaust means. The rotary valve 17 can be eliminated as in the case of the rotary selection valve 12.

Of the discharge port 10 and the exhaust port 11 opened at the top surface of the base portion 2 adjacent to the ridge 3, it is preferable that the exhaust port 11 be located as nearest as possible to the ridge 3, but the discharge port 10 may be opened at a position displaced toward the center of the base portion 2. They may be juxtaposed as shown in FIGS. 1 and 2 or aligned in the longitudinal direction of the slide glass 4 as shown in FIG. 3.

Figure 4:
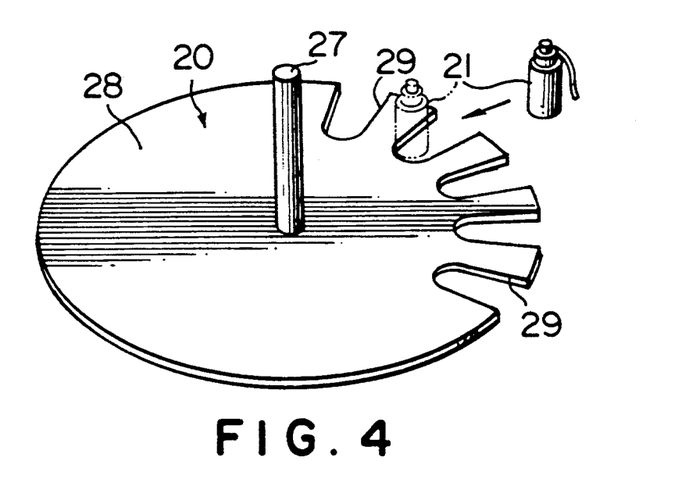
FIG. 4 is a perspective view illustrating a treatment liquid container holder.
Figure 5:
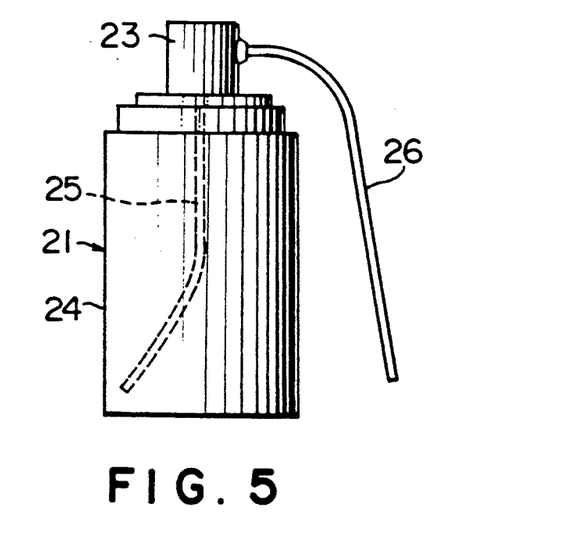
FIG. 5 is a side view of a treatment liquid container.
Figure 6:
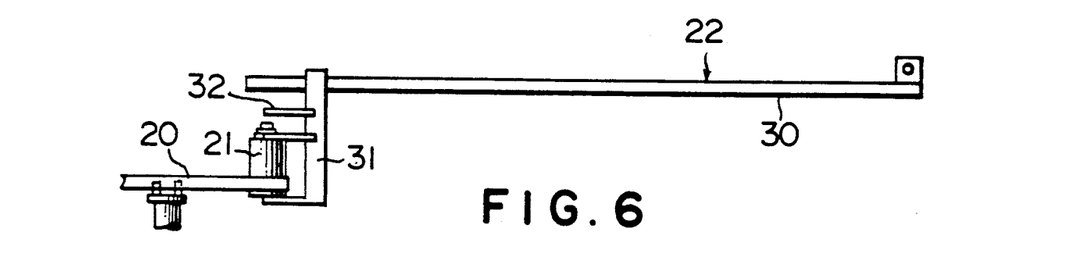
FIG. 6 is a side view of a mechanism including an arm for selecting and manipulating a treatment liquid container.
Figure 7:
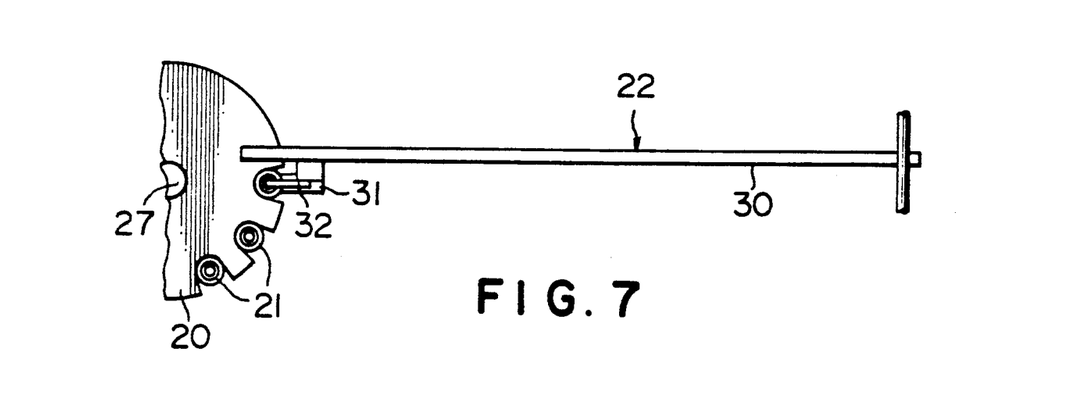
FIG. 7 is a top view thereof.

A liquid dripping means which drips a dyeing liquid over the parts of the upper surface of the base portion 2 which are not covered by the slide glass 4 comprises dyeing liquid containers 21 as shown in FIG. 5 which are supported by a dyeing liquid container holder 20 as shown in FIG. 4, and a dyeing liquid container pickup arm 22 as shown in FIGS. 6 and 7, which arm picks up a dyeing liquid container 21 from its holder 22 and then moves it to a position above a predetermined base portion 2, thereby dripping a dyeing liquid over the exposed surface of the base portion 2.

As shown in FIG. 5, each dyeing liquid container 21 has a push button 23 at the upper end thereof, and when the push button 23 is depressed, the dyeing liquid contained in the container 21 is taken out through hoses 25 and 26 and dripped.

The liquid container holder 20 holds a plurality of such liquid containers 21 one of which is picked up from the holder 20 by the pickup or manipulator arm 22 as described above. The container holder comprises a vertical rotary shaft 27 and a disk 28 securely carried by the rotary shaft 27 for rotation in unison therewith. The disk 28 is formed with a plurality of notches 29 spaced at equal angular distances around the periphery of the disk 28. The dyeing liquid containers 21 made of an elastically deformable material such as a vinyl resin are detachably fitted into the notches 29, respectively.

As described above, the manipulating arm 22 picks up a desired dyeing liquid container 21 from within the notch 29 of the container holder 20 and moves it over a desired base portion 2 upon which is mounted a predetermined slide glass 4 to drip the dyeing liquid onto the exposed surface of the base portion 2. This manipulating arm 22 comprises an arm 30 movable in a horizontal plane, a holding arm 31 attached to the arm 30 in the vicinity of one end thereof, and a depressing arm 32 which is attached to an upper portion of the holding arm 31 so as to be movable vertically. Thus, when the depressing arm 32 moves downwardly, the push button 23 on the upper end of the dyeing liquid container 21 is depressed.

Next, the mode of operation of the preferred embodiment of the present invention with the above-described construction will be described. When a piece of tissue taken from a living body is to be dyed, it is mounted on the slide glass 4, which thereafter has its one end snugly fitted into one of the recesses 7 formed on the upper surface of the bank 6 and is supported by the supporting surface 9 and the ridge 3 in such a way that the piece of tissue mounted on the slide glass 4 is in opposing relationship with the upper surface of the base portion 2. Under this condition, the gap between the undersurface of the slide glass 4 and the upper surface of the base portion 2 diverges in a direction from the ridge 3 toward the supporting surface 9, whereby a thin wedge-shaped gap G is defined as indicated in FIG. 2.

After the slide glass 4 is disposed to bridge the ridge 3 and the supporting surface 9 as described above, the arm 30 of the dyeing liquid container manipulating arm 22 of the dripping means is moved toward the dyeing liquid container holder 20, and the holding arm 31 at one end of the arm 30 holds a desired dyeing liquid container 21 fitted in the notch 29 of the disk 28 of the dyeing liquid holder 20.

After the dyeing liquid container 21 is held by the holding arm 31, the arm is displaced in a horizontal plane to bring the dyeing liquid container 21 to a position above the slide glass 4 upon which is mounted a piece of tissue to be brought into contact with the dyeing liquid.

After the dyeing liquid container 21 has been located at a predetermined position above a predetermined slide glass 4 in the manner described above, the depressing arm 32 at one end of the arm is caused to move downwardly, thereby depressing the push button 23 at the upper end of the container 21. Then, the dyeing liquid is discharged from the container 21 through the hoses 25 and 26 and drips onto the parts of the surface of the base portion 2 exposed at the two sides of the slide glass 4.

The gap G between the upper surface of the base portion 2 and the undersurface of the slide glass 4 which bridges the ridge 3 and the supporting surface 9 diverges from the ridge 3 toward the supporting surface 9 as described above. As a result, the dyeing liquid which drips onto the exposed parts of the surface of the base portion 2 spreads into the thin wedge-like gap G by capillary action and is brought into intimate contact with the piece of tissue mounted on the undersurface of the slide glass 4.

After the piece of tissue mounted on the undersurface of the slide glass 4 and the dyeing liquid are brought into contact with each other for a predetermined time, the rotary valve 16 is so switched that the exhaust port 11 is communicated with the waste liquid tank 19, and thereafter the de-energized exhaust pump 17 is energized so that the waste liquid is discharged from the exhaust port 11 opening adjacent to the ridge 3 into the waste liquid tank 19.

After the exhausting of the dyeing liquid, the exhaust pump 17 is de-energized, and the rotary valve 12 is switched so that the discharge port 10 is communicated with the cleaning liquid storage tank 15 and the feed pump 13 in the cleaning liquid supply means is energized for a predetermined time interval whereby the cleaning liquid is discharged from the discharge port 10 adjacent to the ridge 3.

The cleaning liquid discharged from the discharge port 10 spreads through the gap G between the undersurface of the slide glass 4 and the upper surface of the base portion 2 by capillary action, thereby cleaning or washing away the dyeing liquid adhering to the piece of tissue on the undersurface of the slide glass 4.

After the completion of the cleaning operation for predetermined time interval, the exhaust pump 17 of the waste liquid exhaust means is energized again so as to exhaust the waste cleaning liquid spread through the gap G. Thereafter, the dyeing liquid dripping operation can be carried out.

The above-described steps are repeated to accomplish a predetermined dyeing process.

In the preferred embodiment described above, the rotary valve 12 of the cleaning liquid supply means and the rotary valve 16 are independent, but the operations carried out by both the rotary valves 12 and 16 have a predetermined relationship with each other so that both the valves 12 and 16 can be fabricated as a unitary construction, as will be described in detail hereinafter.

Furthermore, the dyeing liquid supply means is not limited to the type described above in which the dyeing liquid container is moved. The dyeing liquid dripping operation can be equally carried out by providing a plurality of dyeing liquid supply pipe lines arranged above the base portion 2 and dripping a predetermined dyeing liquid through the supply pipe lines.

Moreover, the upper surface of the base portion 2 can be made slightly convex such that the gap between the upper surface of the base portion 2 and the undersurface of the slide glass 4 may be narrowed especially at the exhaust port 11. By doing so, definite exhaust of the used dyeing liquid can be ensured. In addition, when the width of the base portion 2 except the surface thereof upon which the dyeing liquid is dripped, is made narrower than the width of the slide glass, the quantity of the highly expensive dyeing liquid can be further reduced.

With the device for dyeing tissues for immune response observation in accordance with the present invention, the automatic tissue dyeing operation can be carried out with a lesser quantity of the dyeing liquid so that the costs required for immune response observation can be reduced and also the saving in labor can be attained.

Figure 8:
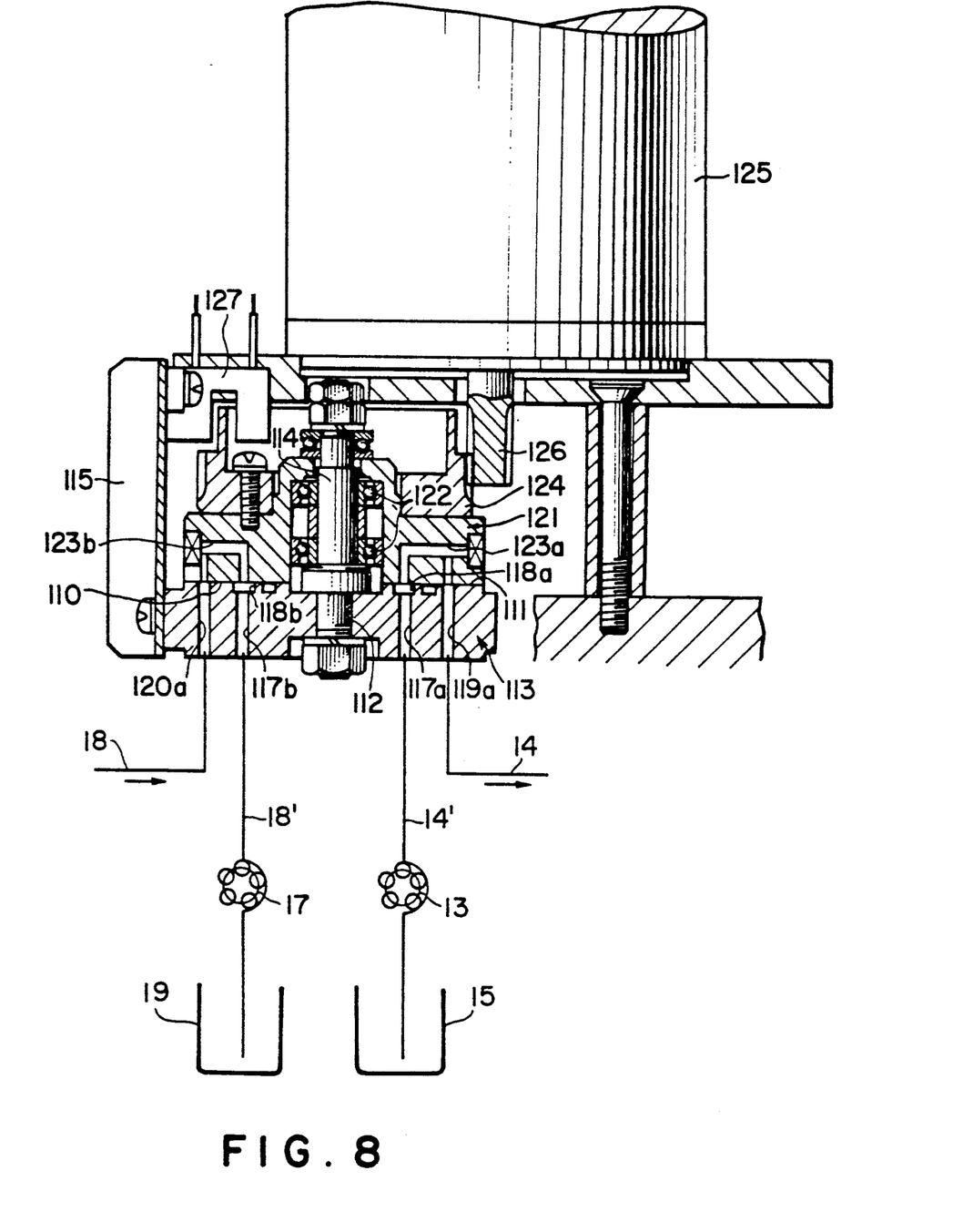
FIG. 8 is a vertical sectional view of a rotary valve which can be used in the present invention.
Figure 9:
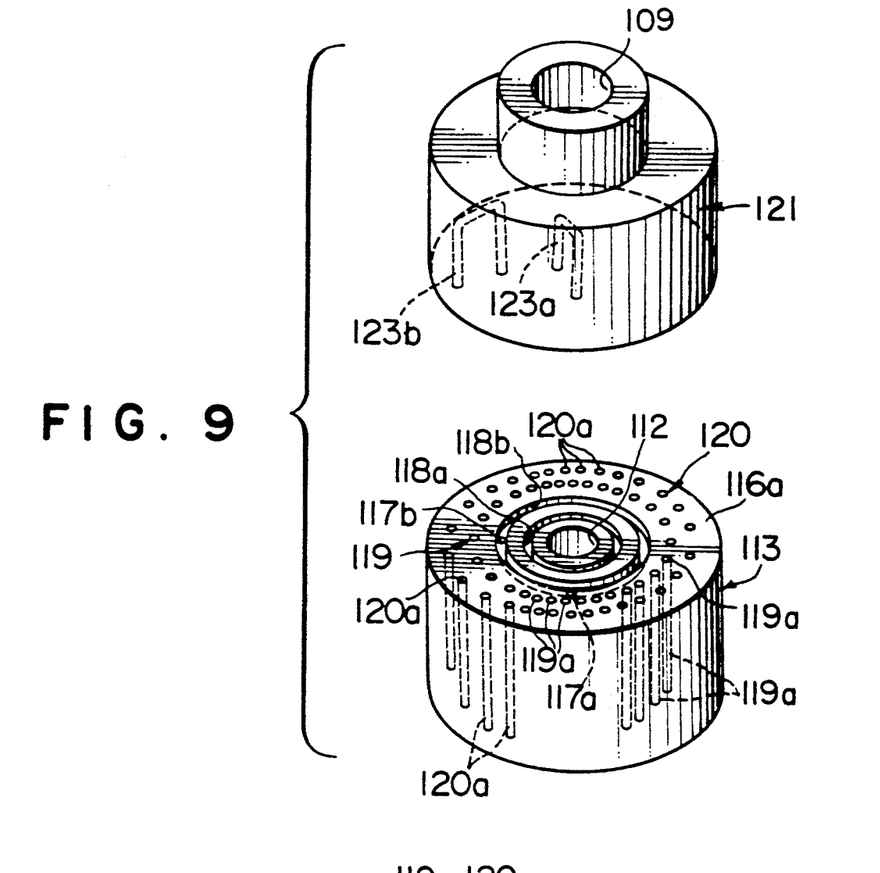
FIG. 9 is an exploded perspective view of the rotary valve, illustrating a stationary valve body and a rotating valve body.
Figure 10:
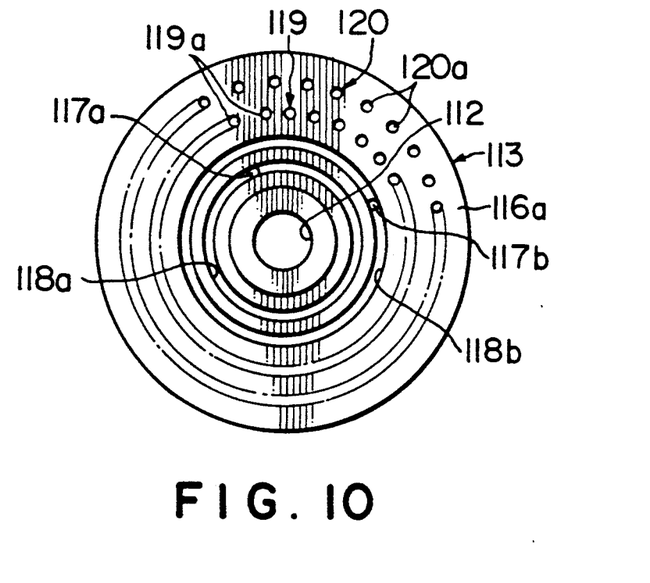
FIG. 10 is a top plan view of the stationary valve body.

Referring next to FIGS. 8 to 10, an example in which the two separate rotary valves 12 and 16 are combined into a unitary construction will be described in detail below.

A stationary valve body 113 in the form of a thick disk has an axially extended through hole 112 into which is fitted a rod or shaft 114. The stationary valve body 113 is secured attached to a supporting plate 115 by passing screws through the wall of the plate 115 and threadably engaging them with tapped holes drilled in the stationary body 113. The shaft 114 has an enlarged-diameter portion at an intermediate part. The outer diameter of this portion is larger than the inner diameter of the through hole 112 and a nut is engaged with the lower end portion of the shaft 114 extended downwardly beyond the bottom surface of the stationary valve body 113, whereby the shaft 114 is securely attached to the stationary valve body 113.

A first flat surface 111 defined over the upper surface of the stationary valve body 113 has first and second liquid passages 117a and 117b, first and second coaxial annular grooves 118a and 118b communicating with the first and second liquid passages 117a and 117b, respectively, and coaxial first and second port groups 119 and 120 each consisting of a plurality of ports 119a (120a).

A plurality of ports 119a of the first port group 119 and a plurality of ports 120 a of the second port group 120 are spaced apart at equal angular distances from each other by 12° and the numbers of the ports 119a and 120a are 30, respectively.

A rotary valve body 121 in the form of a thick disk has a short cylindrical projection extended upwardly from the top surface thereof coaxially thereof as shown in FIG. 8. Furthermore, the rotary valve body 121 has an axially extended through hole 109 into which is fitted the shaft 114 extended from the upper surface of the stationary valve body 113 upwardly and coaxially thereof.

A second flat surface 110 defined at the bottom surface of the rotary valve body 121 is in liquid-tight sliding contact with the first flat surface 111. While the liquid-tight sliding contact between the first and second flat surfaces 111 and 110 is maintained, the rotary valve body 121 is rotatable about the shaft 114 with respect to the stationary valve body 113. The shaft 114 are supported by bearings 122.

Two ends of U-shaped first and second switching passages 123a and 123b are opened in the second flat surface 110. More particularly, one end of the switching passage 123a is in opposing relationship with the first angular groove 118a formed in the first flat surface 111, while the other end of the first switching passage 123a can be aligned with any one of a plurality of the ports 119a of the first port group 119.

In a like manner, one end of the second switching passage 123b is in opposing relationship with the second annular groove 118b while the other end can be aligned with any one of a plurality of the ports 120a of the second port group 120.

At the top surface of the rotary valve body 121, a ring-shaped gear 124 is fitted over the axially extended projection and is in mesh with a gear 126 securely carried by the output shaft of a motor 125 which is mounted on a frame or the like. When the motor 125 is energized for a predetermined time interval, in response to the signal from a control unit (not shown) the rotary valve body 121 carrying the gear 124 is rotated through a predetermined angle; that is, the angular pitch of 12° between the adjacent ports 119a (120a).

A photosensor 127 shown in FIG. 8 has a function of de-energizing and stopping the motor 125 in order to cause the switching passages 123a and 123b to be correctly aligned with the ports 119a and 120a, respectively.

In this rotary switching valve, the first and second annular grooves 118a and 118b in communication with first and second liquid passages 117a and 117b are coaxial with the first and second port groups 119 and 120, respectively, and the angular pitch between the adjacent ports 119a of the first port group 119 is equal to that between the adjacent ports 120a of the second port group 120. The opening at one end of the first switching passage 123a opened at the second flat surface 110 is in an opposing relationship with the first annular groove 118a while the other end can be aligned with one of a plurality of ports 119a of the first port group 119. Furthermore, one end of the second switching passage 123b is in opposing relationship with the second annular groove 118b while the other end can be aligned with one of a plurality of ports 120a of the second port group 120. Therefore, upon rotation of the rotary valve body 121, the first liquid passage 117a is communicated with one of a plurality of ports 119a of the first port group 119 and the second liquid passage 117b is communicated with one of a plurality of ports 120a of the second port group 120.

The rotary switching valve can be incorporated, as shown in FIG. 8, in the device for dyeing tissues for immune response observation of the type described above with reference to FIGS. 1 to 7. That is, one end of a first connecting line 14' having a liquid discharge pump 13 is connected to the lower end opening of the first liquid passage 117a of the stationary valve body 113, while the other end thereof is communicated with a cleaning liquid storage tank 15. On the other hand, one end of a second connecting line 18' having an exhaust pump 17 is connected to the lower end opening of the second liquid passage 117b, while the other end thereof is communicated with a waste liquid tank 19. The ports 119a of the first port group 119a are communicatively connected via discharge pipes 14 with the discharge ports 10 (FIG. 1) opened at the base portions 2 of the dyeing block 1 (FIG. 1), respectively, while the ports 120a of the second port group 120 are communicatively connected via exhaust pipes 18 to discharge ports 11 (FIG. 1) opened at the base portions 2, respectively. When the rotary valve body 121 is rotated through a suitable angle and the discharge pump 17 is energized, used dyeing liquid on one of the base portions 102 can be exhausted through the exhaust port 11 into the waste liquid tank 19. Furthermore, when the exhaust pump 17 is de-energized and the discharge pump 13 is energized, the cleaning liquid stored in the cleaning liquid tank 15 can be discharged through the discharge port 10 formed in the base portion 2. The exhaust of the used cleaning liquid from the base portion 2 is carried out in a manner similar to that described above in connection with the exhaust of the used dyeing liquid.

The rotary switching valve with the above-described construction can reduce the number of valves used.

What is claimed is:

1. A device for dyeing tissues for immune response observation comprising:

flat base means with a substantially horizontal upper surface having first and second sides;

means for supporting on said upper surface a slide glass having an undersurface for facing said upper surface, the undersurface having a tissue attached thereto, said means for supporting the slide glass comprising a ridge-shaped protrusion constructed so as to extend along said first side and a supporting surface constructed so as to extend along the second side, said protrusion and said supporting surface constructed so as to support thereon two end portions of the slide glass, respectively, said protrusion and said supporting surface being disposed and sized such that the protrusion is higher than said upper surface of the flat base means and the supporting surface is higher than said protrusion so as to define thin wedge-shaped capillary gap between said upper surface and said undersurface increasing in width from said first side to said second side; and means for supplying a dyeing liquid into said gap so as to cause the dyeing liquid to spread into the gap by capillary action thereby bringing the liquid into intimate contact with the tissue on the slide glass.

2. The device as claimed in claim 1, further comprising means for positioning the slide glass, said positioning means constructed so as to place the slide glass on the protrusion and the supporting surface.

3. The device as claimed in claim 2 wherein the means for positioning is a recess constructed so as to receive one end of the slide glass.

4. The device as claimed in claim 1, further comprising means for forming waste liquid channels along said first and second sides.

5. The device as claimed in claim 1 wherein said means for supplying a dyeing liquid into the gap comprises means for dripping a dyeing liquid onto the upper surface of the base means.

6. The device as claimed in claim 5 wherein said means for dripping comprises a plurality of dyeing liquid containers, means for holding the containers, and means for selectively moving one of the containers and causing dyeing liquid in said one container to be discharged therefrom for dripping onto the base means.

7. The device as claimed in claim 6 wherein said means for selectively moving of the containers is an manipulator arm means for moving said containers toward and away from the base means and, said manipulator arm means further constructed so as to carry on an end thereof, one of said containers and discharge the dyeing liquid from said one container.

8. The device as claimed in claim 1, further comprising means for supplying a cleaning liquid onto the upper surface of the base means.

9. The device as claimed in claim 8 wherein said means for supplying a cleaning liquid comprises a discharge port opening in the upper surface of the base means, supply pipe means for supplying the cleaning liquid from a cleaning liquid supply source to said discharge port, and valve means in said pipe means.

10. The device as claimed in claim 9, further comprising means for exhausting used dyeing and cleaning liquid from the upper surface of the base means.

11. The device as claimed in claim 10 wherein said means for exhausting comprises an exhaust port opening in the upper surface of the base means, exhaust pipe means connecting the exhaust port to a waste liquid tank, and valve means in said exhaust pipe means.

12. The device as claimed in claim 11 wherein said valve means in the supply pipe means and said valve means in the exhaust pipe means are the same valve means.

* * * * *